United States Patent [19]

Brown et al.

[11] 4,444,883

[45] Apr. 24, 1984

[54] **METHOD FOR THE ISOLATION AND PRESUMPTIVE DIAGNOSIS OF *BACILLUS CEREUS* AND TELLURITE MEDIUM THEREFOR**

[75] Inventors: Robert L. Brown, Irving, Tex.; Thomas B. Platt, Neshanic Station, N.J.

[73] Assignee: E. R. Squibb & Sons, Inc., Princeton, N.J.

[21] Appl. No.: 406,747

[22] Filed: Aug. 9, 1982

[51] Int. Cl.$^3$ .................. C12Q 1/04; C12R 1/085
[52] U.S. Cl. .................... 435/34; 435/834
[58] Field of Search .................. 435/4, 34, 834

[56] References Cited

U.S. PATENT DOCUMENTS 4,308,346  12/1981  Newano .................. 435/34

FOREIGN PATENT DOCUMENTS 2059435  4/1981  United Kingdom .................. 435/34

OTHER PUBLICATIONS

Bergey's Manual of Derminative Bacteriology, 8th Ed., pp. 534–535, 1974.
S. Finrgold et al., Bailey and Scott's Diagnostic Microbiology, 5th Ed., pp. 20 and 21; 1978.
Donovan, K. O., "A Selective Medium for *Bacillus cereus* in Milk," J. Appl. Bacteriol., 21:100–103 (1958).
Kim et al., "Occurrence of *Bacillus cereus* in Selected Dry Food Products," J. Milk Food Technol. 34:12–15 (1971).
Kim et al., "Enumeration and Identification of *Bacillus cereus* in Foods," Appl. Microbiol., 22:581–587 (1971).
Mossel, et al., "Enumeration of *Bacillus cereus* in Foods," Appl. Microbiol., 15:650–653 (1967).
Fleming, A. F., "On the Specific Antibacterial Properties of Penicillin and Potassium Tellurite," J. Pathogenic. Bacteriol., 35:831–842 (1932).
Zebovitz et al., "Tellurite–Glycine Agar:A Selective Plating Medium for the Quantitative Detection of Coagulase-Positive Staphylococci," J. Bacteriol., 70:686–690 (1955).

*Primary Examiner*—Robert J. Warden
*Assistant Examiner*—W. J. Herald
*Attorney, Agent, or Firm*—Lawrence S. Levinson; Burton Rodney

[57] ABSTRACT

A method is provided for the isolation and presumptive diagnosis of *Bacillus cereus* which method is useful in the assay of antibiotic preparations, food products such as milk, drug products and cosmetics. A medium for use in such method is also provided which medium includes tellurite, glycine and polymyxin, and inhibits most organisms which grow and resemble *Bacillus cereus* on this medium. If an organism grows on the medium and has characteristic colonies, a presumptive diagnosis of *Bacillus cereus* can be assumed until further tests are made.

9 Claims, No Drawings

METHOD FOR THE ISOLATION AND PRESUMPTIVE DIAGNOSIS OF *BACILLUS CEREUS* AND TELLURITE MEDIUM THEREFOR

FIELD OF THE INVENTION

The present invention relates to a method for the isolation and presumptive diagnosis of *Bacillus cereus* and to a medium for use in such method.

BACKGROUND OF THE INVENTION

Strains of *Bacillus cereus* have been implicated in cases of food poisoning in humans and in bovine mastitis coming, in some instances, from antibiotics used in treatment. Thus, a medium for the rapid presumptive diagnosis of *Bacillus cereus* would indeed be useful. In fact, several such media have been described including egg yolk, citrate, lithium chloride and polymyxin, as described by Donovan, K. O., "A Selective Medium for *Bacillus cereus* in Milk", J. Appl. Bacteriol., 21:100-103 (1958); mannitol, egg yolk and polymyxin, as described by Kim et al., "Occurrence of *Bacillus cereus* in Selected Dry Food Products", J. Milk Food Technol. 34:12-15 (1971); egg yolk and polymyxin as described by Kim et al., "Enumeration and Identification of *Bacillus cereus* in Foods", Appl. Microbiol. 22:581-587 (1971); and mannitol, egg yolk and phenol red agar as described by Mossel, et al., "Enumeration of *Bacillus cereus* in Foods," Appl. Microbiol., 15:650-653 (1967).

The above media are all egg yolk containing media. Unfortunately, unless such media are handled with extreme care, a troublesome spreading problem may result.

The use of tellurite as an inhibitor was reported by Fleming, A. F., "On the Specific Antibacterial Properties of Penicillin and Potassium Tellurite", J. Pathogenic. Bacteriol., 35:831-842 (1932). Zebovitz et al. report the use of tellurite (and 3% glycerine) for coagulase positive staphylococci, in "Tellurite-Glycine Agar:A Selective Plating Medium for the Quantitative Detection of Coagulase-Positive Staphylococci", J. Bacteriol, 70:686-690 (1955).

DESCRIPTION OF THE INVENTION

As indicated, *Bacillus cereus* has been found to be responsible for outbreaks of food poisoning in many parts of the world. It would thus be of enormous value to be able to follow the proliferation of *Bacillus cereus* in foods, drugs, cosmetics and the like so as to establish, before any disease may occur, that the food or other comestible or cosmetic may become dangerous upon further storage.

In accordance with the present invention, a method is provided for the isolation and presumptive diagnosis of *Bacillus cereus* in milk, antibiotic preparations, other food and drug products or cosmetics, which method includes the steps of preparing a non-egg yolk-containing medium for growth of *Bacillus cereus* which inhibits most organisms which grow and resemble *Bacillus cereus* on such medium, the medium including tellurite, glycine and polymyxin, and assaying a product such as described above employing said medium to isolate *Bacillus cereus*, if present in said assayed product, on said medium, and allowing for presumptive diagnosis of *Bacillus cereus*. Thus, if an organism grows on the medium and has characteristic colonies, a presumptive diagnosis of *Bacillus cereus* can be assumed until further tests are made. The method of the invention is effective in differentiating *Bacillus cereus* from similarly appearing organisms. However, the final diagnostic criteria must be made only after other differential tests have been completed. Notwithstanding the above, it is still extremely useful to have a rapid presumptive procedure as described herein which employs a medium which does not contain egg yolk and therefore does not promote spreading.

In addition, in accordance with the present invention, an agar (non-egg-yolk containing) medium is provided which includes in addition to agar and other conventional nutrients, tellurite preferably in the form of potassium tellurite, glycine and polymyxin, and optionally mannitol.

The tellurite will be present in an amount within the range of from about 0.005 to about 0.02% and preferably from about 0.01 to about 0.015% by weight of the medium. The presence of more than about 0.01% by weight tellurite is unnecessary and will have no bearing on organism inhibition while the presence of less than about 0.005% by weight tellurite will allow for growth of black colonies which are characteristic of but different from *Bacillus cereus* colonies.

The glycine will be present in the medium in a weight ratio to the tellurite of within the range of from about 2500:1 to about 3000:1 and preferably from about 2900:1 to about 3000:1 and in an amount within the range of from about 2 to about 4% and preferably from about 2.5 to about 3.5% by weight of the medium. Where less than about 1.5% glycine is present, certain staphylococci will grow on tellurite-containing media with the colonies somewhat resembling *Bacillus cereus* (small, black). However, the presence of more than 3% by glycine is unnecessary and will not add to the efficacy of the invention.

Polymyxin will be present in the medium of the invention in a weight ratio to the tellurite of within the range of from about 0.05:1 to about 0.2:1 and preferably from about 0.09:1 to about 0.1:1 and in an amount within the range of from about 0.0005 to about 0.0015% and preferably from about 0.0009 to about 0.001% by weight. Where less than about 0.0001% by weight polymyxin is present, the medium could support the growth of other organisms. However, the presence of more than about 0.001% by weight polymyxin is unnecessary and produces no significant advantages.

Mannitol fermentation (acid) may be included in the medium of the invention in amounts within the range of from about 0.4 to about 0.6% and preferably from about 0.49 to about 0.51% by weight. The mannitol will indicate growth of organisms which may ferment mannitol.

The medium of the invention will also contain from about 1 to about 2% by weight agar and/or other conventional nutrients for supporting the growth of *Bacillus cereus*. Examples of such materials which may be present in the agar include, but are not limited to, surfactants such as Tween 20, as well as phenol red, serum, and the like.

In carrying out the method of the invention, the tellurite-glycine-polymyxin agar medium is prepared. Thereafter, the material to be assayed is grown on the medium employing the following procedure.

Inoculate enrichment medium with 1.0 to 10.0 ml of an appropriate sample (food, drug or other sample). Incubate 24 hours at 37° C., and observe for growth. Inoculate tellurite-glycine-polymyxin agar plates with 0.1 ml of enrichment medium, spread the inoculum, and again incubate at 37° C. until growth is observed. Inoculation can be made to plates direct from samples, if desired, omitting the enrichment.

The agar medium is then observed for the presence of colonies and colonial characteristics, particularly black coloration of colonies which indicate *Bacillus cereus.*

EXAMPLE

The following experiments were carried out to illustrate the method for the isolation and presumptive diagnosis of *Bacillus cereus.*

| Materials | | |
|---|---|---|
| 1. Organisms used | | |
| All organisms bearing S.C. designation (Squibb culture) have been thoroughly classified in Squibb Laboratories. Others are well known strains. | | |
| 2. Media: | | |
| A. Enrichment Medium | | |
| Brain Heart Infusion (BBL) | 37 | g |
| Glycine | 30 | g |
| Tween 20 | 100 | g |
| Water | + 0 1000 | ml |
| Sterilize at 121.5° C. for 15 miniutes, (cool to 50° C.) and add 1 ml of a 10,000 mcg/ml solution of filter sterilized polymyxin B sulfate. Dispense 50 ml to sterile 250 ml cotton stoppered Erlenmeyer flasks. | | |
| B. Tellurite-Glycine-Polymyxin Agar | | |
| Trypticase Soy Broth (BBL-No dextrose) | 27.5 | g |
| Agar Granulated (BBL) | 15.0 | g |
| Mannitol | 5.0 | g |
| Glycine | 30.0 | g |
| Phenol Red | 0.018 | g |
| Water | to 940.0 | ml |
| Mix and sterilize at 121.5° C. for 15 minutes; cool to 50° C. and add: | | |
| Sterile 10,000 mcg/ml polymyxin B sulfate | 1.0 | ml |
| Sterile Human Serum | 50.0 | ml |
| Sterile 1% Potassium Tellurite Solution | 10.0 | ml |
| Pour 20 ml into 100 mm Petri plates. | | |
| C. Brain Heart Infusion Broth | | |
| Brain Heart Infusion | 37.0 | g |
| Distilled water | to 100.0 | ml |
| Dissolve and dispense 20 ml to 1 × 6" screw cap tubes. Sterilize at 121.5° C. for 15 minutes. | | |
| D. Tellurite Agar without Glycine | | |
| Medium B without glycine | | |
| E. Saline | | |
| 0.9% NaCl in water. | | |
| 3. Filter System | | |
| Use a Nalgene No. 120, 0.2 M | | |

Methods

1. Samples

A. Antibiotic Powder—use 1 g

B. Cloxacillin Syringes—use contents (6 ml)

C. Fungizone Oral Suspension—use 10 ml of reconstituted powder

D. Cultures—1 ml of BHI grown cells to Medium A or 0.5 ml to Medium B

2. Culture Methods

A. Stock Culture Broth

Inoculate Medium C with a loop of stock culture and incubate at 37° C. for 24 hours.

B. Enrichment Culture

Inoculate Medium A with sample as above. Incubate 24 hours at 37° C. on a flask shaker.

Where desired, 1.0 ml of Penicillinase Solution (BBL-$10^6$ $\mu$/ml) can be added for cloxacillin syringe culture.

C. Tellurite Agar Culture

Inoculate plates with 0.5 ml of Enrichment Broth or Stock culture broth, spread with a glass rod, and incubate at 37° C.

3. Test readings

A. Broth

Observe flasks or tubes for turbidity.

B. Agar

Observe plates for the presence of colonies and colonial characteristics, particularly black coloration of colonies. Observe areas around colonies for clear zones in the red agar, indicating mannitol fermentation.

4. Sensitivity of the Method

Serially dilute *B. cereus* ATCC 11778, in Medium C to $10^9$, in sterile physiological saline (Medium E). Transfer 1.0 ml of each dilution to tubes containing 10 ml molten BHI Agar, cooled to 50° C. Mix and pour into 100 mm Petri plates. Incubate overnight and count colonies. Transfer 1.0 ml from each dilution to the contents of a cloxacillin syringe contained in separate sterile blender flasks (100 ml). Blend 30 seconds and add 50 ml Medium A. Again blend for 30 seconds. Transfer each of the contents to separate sterile 250 ml Erlenmeyer flasks and incubate overnight at 37° C. Observe for growth and transfer 0.5 ml of each flask to separate plates of Medium B. Again, incubate at 37° C., but observe plates for growth for up to 72 hours.

Results

As shown in Table One, many organisms similar to *B. cereus* did not grow in the presence of polymyxin (Medium A). In addition, the presence of tellurite was inhibitory to still other organisms. Of these organisms which can grow on Media A and B, most are readily differentiated from *B. cereus* by colonial appearance. The remaining few are further differentiated by mannitol fermentation (acid).

Certain of the staphylococci grow on tellurite-containing media with the colonies somewhat resembling *B. cereus* (small, black). To separate these strains from *B. cereus,* glycine was added at 3%. Table Two shows growth on Medium B with and without glycine, compared to growth of *B. cereus.* Should growth of other strains be found, mannitol fermentation would again be a useful differential test.

Table Three shows the potential usefulness of tellurite-glycine medium in isolation of *B. cereus* from antibiotic preparations with and without the addition of *B. cereus.* In addition, milk can also be evaluated for the presence of *B. cereus* by the same method.

Sensitivity of the method, comparing plate counts of serial dilutions on Brain Heart Infusion Agar to antibiotic samples to which serially diluted *B. cereus* had been added, indicates a sensitivity of less than five cells/sample.

In order to determine typical *B. cereus* cells on tellurite-glycine-polymyxin Medium B, *B. cereus* cells were prepared by extrusion of a sample, in Medium A, of spiked cloxacillin syringes through an 0.2/$\mu$ filter (syringe type). Black colonies indicate *B. cereus,* while the gray colonies, by microscopy, are fungi. Since these syringes (see method 4), were spiked at a level of five cells/syringe, the sensitivity of the method is confirmed.

TABLE ONE

GROWTH AND APPEARANCE OF MICROORGANISMS ON TELLURITE MEDIA

| Test No. | Organism | ATCC Number | Squibb Number | Growth Medium A | Growth Medium B | Appearance On Medium B | Medium Acid From Mannitol |
|---|---|---|---|---|---|---|---|
| 1 | Bacillus cereus | 13061 | 8598 | + | + | SB | None |
| 2 | B. cereus | 11778 | 8613 | + | + | SB | None |
| 3 | B. circulans | — | 1834 | NG | NG | NG | — |
| 4 | B. coagulans | 7050 | 9261 | NG | NG | NG | — |
| 5 | B. megaterium | 14946 | 3782 | + | + | LG | + |
| 6 | B. megaterium | 10778 | 3783 | NG | NG | NG | — |
| 7 | B. polymyxa | NRRL-B-510 | 1522 | + | + | SB | + |
| 8 | B. pumilis | 14884 | 8513 | NG | NG | NG | — |
| 9 | B. subtilis | 6633 | 1355 | NG | NG | NG | — |
| 10 | B. subtilis | NRRL-558 | 1659 | NG | NG | NG | — |
| 11 | B. subtilis | 12139 | 3882 | + | + | SB | + |
| 12 | B. subtilis (var. niger) | 6455 | 3409 | + (trace) | NG | NG | — |
| 13 | B. thuringensis | 10792 | 2928 | NG | NG | NG | — |
| 14 | Corynebacterium xerosis | NCTC 9755 | 3638 | + | + | LG | ND |
| 15 | C. acnes | 6919 | 4020 | + | + | LG | ND |
| 16 | Brevibacterium ammoniagena | 6872 | 9149 | + | + | Brown | ND |
| 17 | B. cereus | — | local isolant | + | + | SB | None |
| 18 | B. cereus | — | Philpot Number 1 (local isolant) | + | + | SB | None |
| 19 | Saliva Control (for Streptococcus sp) | — | — | + | one colony | White (yeast) | None |

Code: SB = small, black colonies (1-3 mm); LG = large, gray colonies (>5 mm); NG = No growth; ND = not determined

TABLE TWO

GROWTH APPEARANCE OF STAPHYLOCOCCUS AUREUS AND B. CEREUS ON TELLURITE MEDIA

| Organism | ATCC Number | SC Number | Growth on Medium B Glycine | No Glycine | BHI Agar (BBL) |
|---|---|---|---|---|---|
| Staphylococcus aureus | — | 2399 | 0 | + | + |
| S. aureus | — | 1579 | 0 | + | + |
| S. aureus | — | 9578 | 0 | + | + |
| S. aureus | — | 9601 | 0 | + | + |
| S. aureus | — | local isolant | 0 | + | + |
| B. cereus | 10361 | 8598 | + | + | + |
| B. cereus | 11778 | 8613 | + | + | + |
| B. cereus | — | Philpot #1 | + | + | + |

TABLE THREE

CONTAMINATION OF PRODUCTS BY B. CEREUS

| Sample Number | Contents | Growth Medium A | Medium B |
|---|---|---|---|
| 1 | FOS | NG | NG |
| 2 | FOS | NG | NG |
| 3 | FOS | NG | NG |
| 4 | FOS | NG | NG |
| 5 | FOS$^a$ | + | SB |
| 6 | FOS$^a$ | + | SB |
| 7 | Ampho | NG | NG |
| 8 | Ampho$^a$ | + | SB |
| 9 | Clox | NG | NG |
| 10 | Clox | NG | NG |
| 11 | Clox | NG | NG |
| 12 | Clox | NG | NG |
| 13 | Clox$^a$ | + | SB |
| 14 | Clox$^a$ | + | SB |
| 15 | Clox$^a$ | + | SB |
| 16 | Clox$^a$ | + | SB |
| 17 | Milk$^a$ | + | SB |
| 18 | Milk$^a$ | + | SB |

CODE:
FOS = E. R. Squibb & Sons, Inc. Fungizone for Oral Suspension - Batch Number 174KL
Ampho = E. R. Squibb & Sons, Inc. Amphotericin Powder - FGNX-17-CP
Clox = 250 mg cloxacillin in 6 ml peanut oil, E. R. Squibb & Sons, Inc. Cloxacillin Syringe for Udder Infusion
$^a$ = spiked with approximately five cells of B. cereus ATCC 11778 per dose 1 g or one syringe (6 ml)
SB = small, black colonies

What is claimed is:

1. A method for the isolation and presumptive diagnosis of *Bacillus cereus* which comprises preparing an agar medium for growth of *Bacillus cereus* which medium is free of egg yolk and comprises a tellurite salt, glycine and polymyxin, the tellurite salt, glycine and polymyxin being present in amounts which inhibit most organisms which grow and resemble *Bacillus cereus* on such medium, growing a sample on said medium employing said medium to isolate *Bacillus cereus,* determining the presence of *Bacillus cereus* whereby a presumptive diagnosis of *Bacillus cereus* can be made if an organism grows on the medium.

2. The method as defined in claim 1 wherein the tellurite salt is potassium tellurite.

3. The method as defined in claim 1 wherein the tellurite salt is present in an amount within the range of from about 0.01 to about 0.015% by weight of the medium.

4. The method as defined in claim 1 wherein the glycine is present in an amount within the range of from about 2 to about 4% by weight of the medium.

5. The method as defined in claim 1 wherein the polymyxin is present in an amount within the range of from about 0.0005 to about 0.0015% by weight of the medium.

6. The method as defined in claim 1 wherein the medium further includes mannitol, phenol red, serum, trypticase soy, and agar.

7. The method as defined in claim 1 wherein the glycine is present in a weight ratio to the tellurite of within the range of from about 2500:1 to about 300:1 and the polymyxin is present in a weight ratio to the tellurite of within the range of from about 0.09:1 to about 0.1:1.

8. The method as defined in claim 1 wherein said sample to be grown on said medium is a food product, drug product or cosmetic.

9. The method as defined in claim 8 wherein said sample to be grown on said medium is an antibiotic preparation or milk.

* * * * *